US010548746B2

(12) United States Patent
Blanc (10) Patent No.: US 10,548,746 B2
(45) Date of Patent: Feb. 4, 2020

(54) LOCKING AND UNLOCKING DEVICE FOR A KNEE PROSTHESIS (71) Applicant: Henri Blanc, Leognan (FR)

(72) Inventor: Henri Blanc, Leognan (FR)

(*) Notice: Subject to any disclaimer, the term of this patent is extended or adjusted under 35 U.S.C. 154(b) by 136 days.

(21) Appl. No.: 15/735,711

(22) PCT Filed: Jun. 13, 2016

(86) PCT No.: PCT/FR2016/051420
§ 371 (c)(1),
(2) Date: Dec. 12, 2017

(87) PCT Pub. No.: WO2016/198808
PCT Pub. Date: Dec. 15, 2016

(65) Prior Publication Data
US 2018/0168828 A1 Jun. 21, 2018

(30) Foreign Application Priority Data

Jun. 12, 2015 (FR) .................................... 15 55376

(51) Int. Cl.
A61F 2/64 (2006.01)
A61F 5/01 (2006.01)
A61F 2/68 (2006.01)
A61F 2/50 (2006.01)

(52) U.S. Cl.
CPC .............. A61F 2/64 (2013.01); A61F 5/0125 (2013.01); A61F 2002/507 (2013.01); A61F 2002/5043 (2013.01); A61F 2002/5069 (2013.01); A61F 2002/5073 (2013.01); A61F 2002/6845 (2013.01); A61F 2002/6854 (2013.01); A61F 2002/6872 (2013.01)

(58) Field of Classification Search
CPC ................ A61F 2/64–2002/648; A61F 5/0125
See application file for complete search history.

(56) References Cited

U.S. PATENT DOCUMENTS 5,031,606 A * 7/1991 Ring, Sr. ............... A61F 5/0125
602/16
7,087,091 B1 8/2006 Chen
8,715,367 B1 5/2014 Pansiera et al.

FOREIGN PATENT DOCUMENTS

| EP | 2502607 | 9/2012 |
|----|---------|--------|
| FR | 2972920 | 9/2012 |
| GB | 344430  | 3/1931 |

OTHER PUBLICATIONS

International Search Report, dated Sep. 8, 2016, priority document.

* cited by examiner

Primary Examiner — David H Willse
(74) Attorney, Agent, or Firm — Greer, Burns & Crain, Ltd.

(57) ABSTRACT

A locking/unlocking device for a knee prosthesis, comprising a femoral section and a tibial section provided with a tibial plate. These two femoral and tibial sections are both rotatably mounted, coaxial about an axis, comprising a disk constituting the femoral section, two left and right flanges, and a through-shaft, a freewheel assembly comprises a pinion provided with ramps and one rolling member per ramp, an unlocking arrangement comprising a wheel with pins, and a part remote from the unlocking arrangement comprising an angular control comprising at least one connecting rod interposed between the remote part and the tibial plate.

14 Claims, 12 Drawing Sheets

LOCKING AND UNLOCKING DEVICE FOR A KNEE PROSTHESIS

CROSS-REFERENCES TO RELATED APPLICATIONS

This application claims the benefit of the French patent application No. 1555376 filed on Jun. 12, 2015, the entire disclosures of which are incorporated herein by way of reference.

BACKGROUND OF THE INVENTION

The present invention relates to a locking/unlocking device for a knee prosthesis, operating by means of the wearer's energy alone, usable especially in cases of femoral amputation.

There are many sophisticated devices using hydraulic cylinder systems with solenoid valves driven from information given by sensors, incorporating microprocessors. Due to the presence of systems using electrical means, it is necessary to provide a source of electrical energy and a means of recharging the source.

These sophisticated devices make it possible to make very accurate adjustments but they have many drawbacks; in particular, they are complex and costly or even very costly.

In countries that have a well-developed medical infrastructure, amputations are performed, particularly, as a result of accidents or chronic vascular disease associated with diabetes, and on some people with low muscular potential who are seeking means of walking more safely.

In countries with limited medical infrastructure, access to sophisticated prostheses is even more difficult.

French patent FR 2 972 920 discloses a control device for a knee prosthesis for a leg.

This control device is fully mechanical and very compact. It requires only low maintenance and is more affordable.

Such a control device is suitable for applications in large numbers, particularly intended for children.

To achieve this goal there are two articulated sections that rotate in relation to each other. One of these is the femoral section secured to the amputated part of the femur via any suitable means, and the other is the tibial section which receives an artificial shin and foot in a manner known per se.

The purpose of this prosthesis of the prior art is to ensure at least one freedom of the rotating joint when the wearer raises his/her leg and when the latter is not supported on the ground, and blocks rotation when the leg is supported on the ground, to allow the body to tilt forward, generating as natural a walking movement as possible for the wearer.

This prosthesis of the prior art proposes a solution incorporating a freewheel and means of controlling the freewheel. These control means are controlled by a cable mounted on two pulleys with a pretensioning spring and a movable plate which stretches or relaxes the cable making it possible to block or release the freewheel.

Mounting these cable control means is a tricky operation requiring an adjusted cable, and a cable pretensioning spring or similar means.

SUMMARY OF THE INVENTION

A purpose of the present invention is to provide a solution for controlling the freewheel and thereby controlling locking and unlocking, which is simple, easy to manufacture, very easy to assembly and makes the prosthesis so equipped even more reliable.

A variant also allows sitting and standing up, bearing on the prosthetic leg, the prosthesis moving to walking mode automatically as soon as the wearer has reached standing position.

BRIEF DESCRIPTION OF THE DRAWINGS

The locking/unlocking device for a knee prosthesis according to the present invention is now described in detail according to a preferred non-restrictive embodiment, with reference to the attached drawings, in which the various figures represent.

DETAILED DESCRIPTION OF THE PREFERRED EMBODIMENTS

Figure 1:
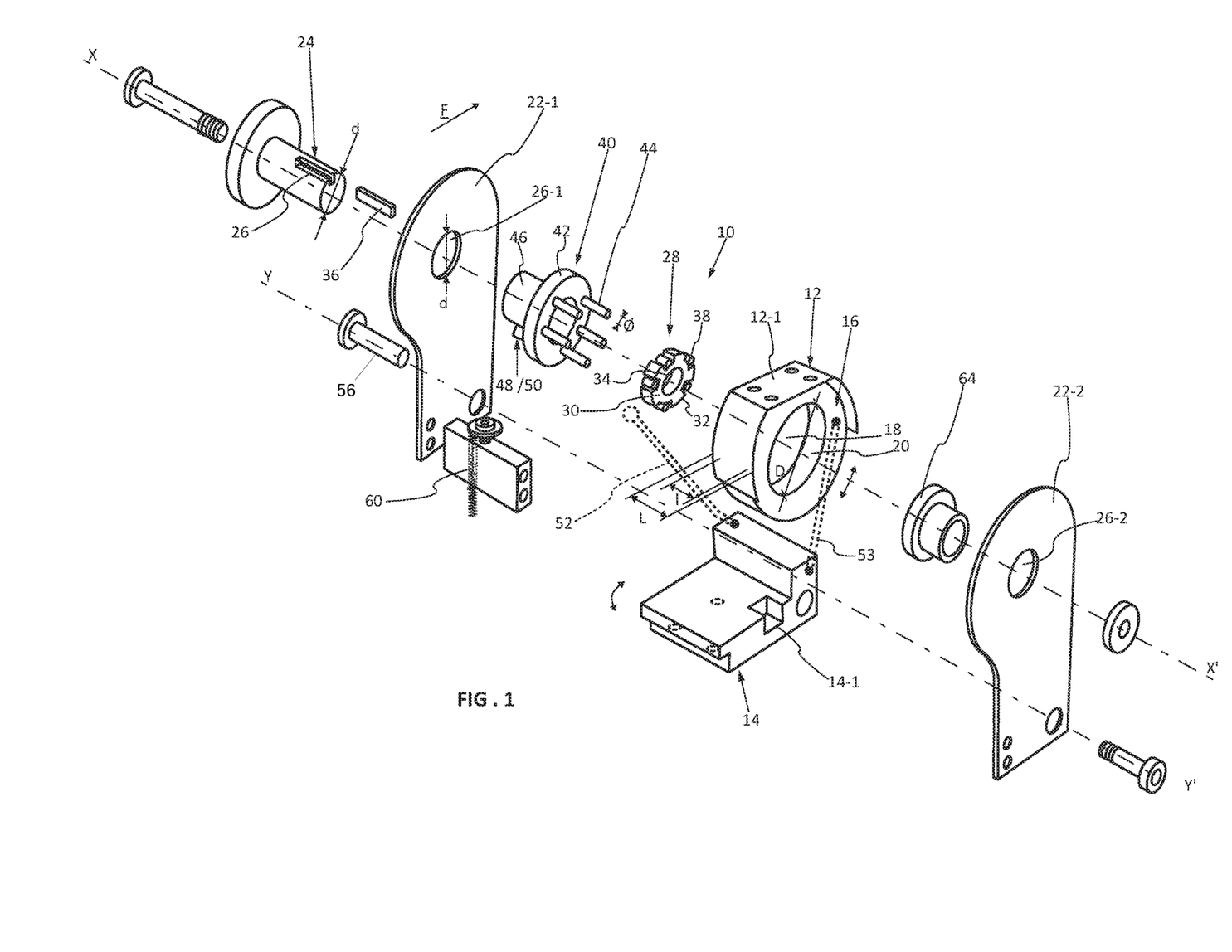
FIG. 1: a schematic perspective exploded view of the knee prosthesis according to the present invention, with its locking/unlocking mechanism.
Figure 2:
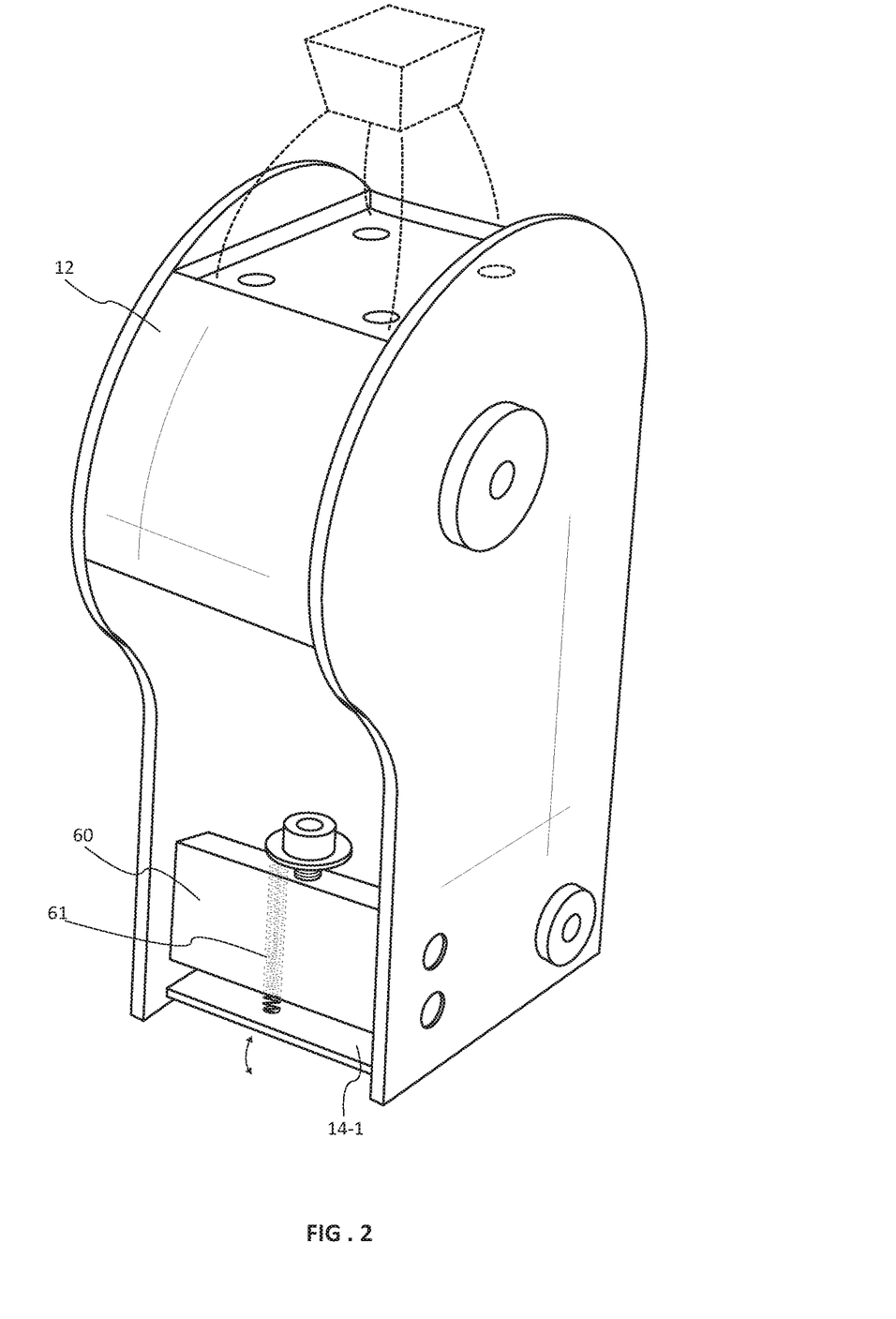
FIG. 2: a view of the prosthesis of FIG. 1, mounted.
Figure 3:
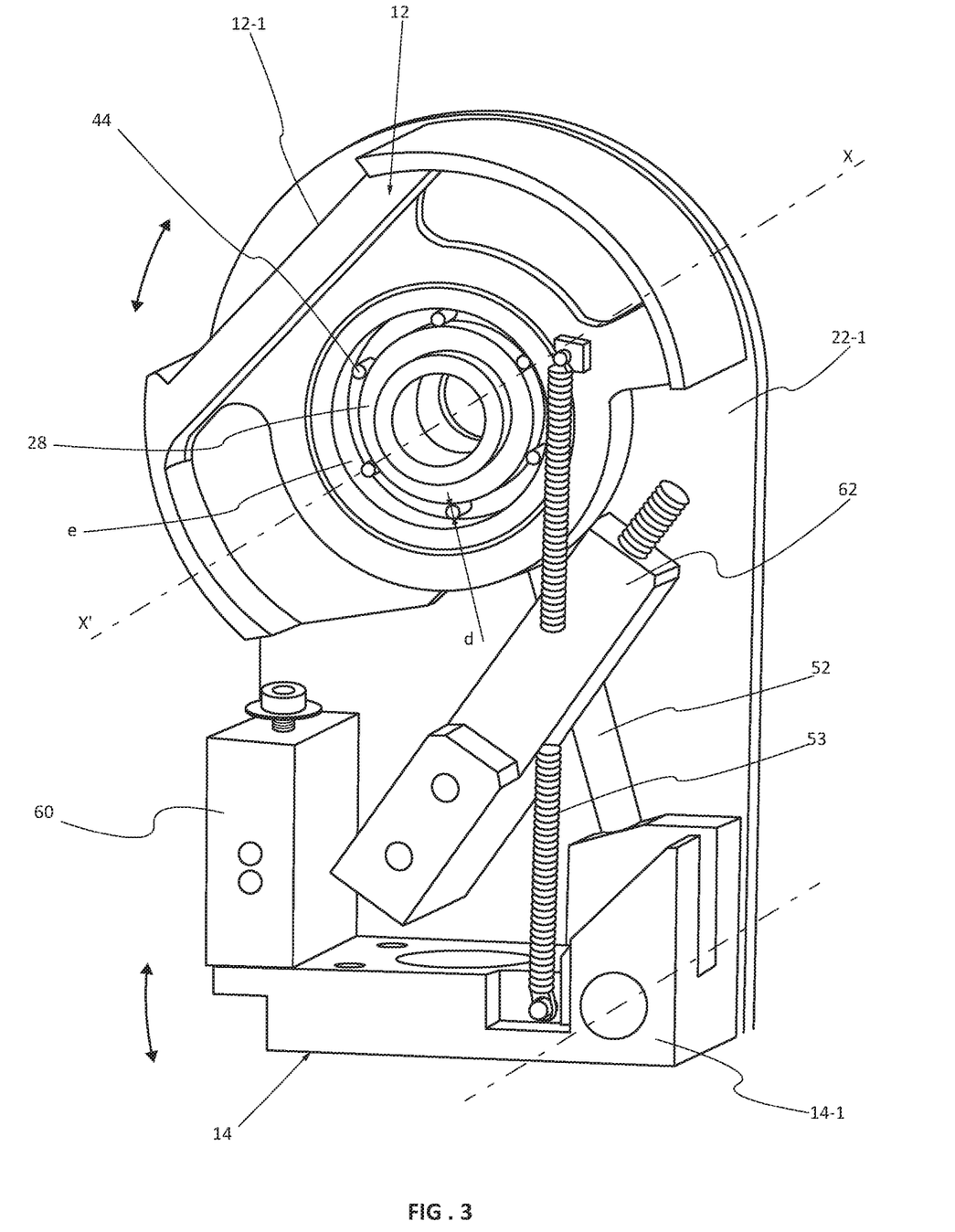
FIG. 3: a view of the prosthesis of FIG. 1, with the right flange removed.

FIGS. 1, 2 and 3 show the locking/unlocking device for a knee prosthesis according to the present invention, this prosthesis 10 comprising a femoral section 12 and a tibial section 14.

The femoral section 12 is intended to be connected to the wearer's thigh, not shown, by any suitable means, not included in the present invention, only a femoral fixation plate 12-1 and a tibial fixation plate 14-1 being provided for the necessary mechanical connections with these suitable means.

The femoral 12 and tibial 14 sections are both rotatably mounted, coaxial about an axis XX', corresponding to the natural axis of bending of the knee.

The femoral part 12 comprises a cylindrical part 16, of width L, having all the recesses and trimming necessary to lighten it, whose central axis is coaxial with axis XX'.

The upper part of this disc carries the fixing plate 12-1 intended to receive means of connection to the wearer's thigh as indicated above, these fixing means in this case consisting of a flattened part on the upper outer part of the radial surface of the cylindrical part 16, having tapped bores to receive screws, for example.

This cylindrical part 16 comprises a central, cylindrical housing 18, arranged coaxially with axis XX'.

This central, cylindrical housing 18 therefore comprises a track 20 of width 1, less than width L the cylindrical part 16 and of diameter D.

The tibial section 14 includes, in particular, two left and right flanges, 22-1 and 22-2, and a single through-shaft 24, mounted in the corresponding holes 26-1 and 26-2 formed in the flanges, this single through-shaft 24 being also coaxial with axis XX'.

This through-shaft 24 has a diameter d, less than D, freeing an annular space E. This through-shaft 24 comprises a longitudinal groove 26, arranged along a generating line.

Between the edge of this shaft 24 and the track 20 of the disc, there is a freewheel assembly 28, in this case a roller type freewheel.

This freewheel assembly 28 comprises a pinion 30 provided with ramps 32, also carrying a spline 34 of profile conjugate with spline 26 of through-shaft 24, a key 36 providing angular immobilization of the pinion 30 with ramps 32 on the through-shaft.

Pinion 30 with ramps and through-shaft 24 are also coaxial with axis XX'.

After assembly, the edge of ramps 32 frees a space less than E.

A roller 38 is placed between each ramp of the pinion and track 20 of the disk, the diameter of these rollers being greater than the distance separating the upper part of the ramp and the track 20, and less than the distance separating the lower part of the ramp from this same track 20.

In one direction, each roller may become jammed between its ramp 32 and track 20, providing a temporary mechanical rotational connection between the disc and the tibial section. In the other direction, each jammed roller becomes unjammed and frees rotational movement between the disc and the tibial section.

Means 40 are also provided to permanently unlock rollers 38, as can be seen in FIGS. 1, 2 and 3.

These unlocking means 40 comprise a wheel 42 with pins 44, also mounted coaxial with axis XX'. The number of pins 44 is equal to the number of ramps 32 and rollers 38.

This wheel 42 with pins 44 is rotatably mounted around the through-shaft 24.

Pins 44 are oriented parallel to generating lines of the through-shaft 24.

These pins 44, preferably in the form of a cylinder, are supported only by one end, and they penetrate the annular space e, located between the outer edge of ramps 32 and track 20. The diameter 0 of these pins is smaller than dimension e.

These pins have a length such that they come in line with the ramps without exceeding their width.

This wheel 42 with pins 44 comprises an offset section 46 between the cylindrical part 16 and the left flange 22-1.

This one-piece, offset section 46, receives angular control means 48.

Figure 4A:
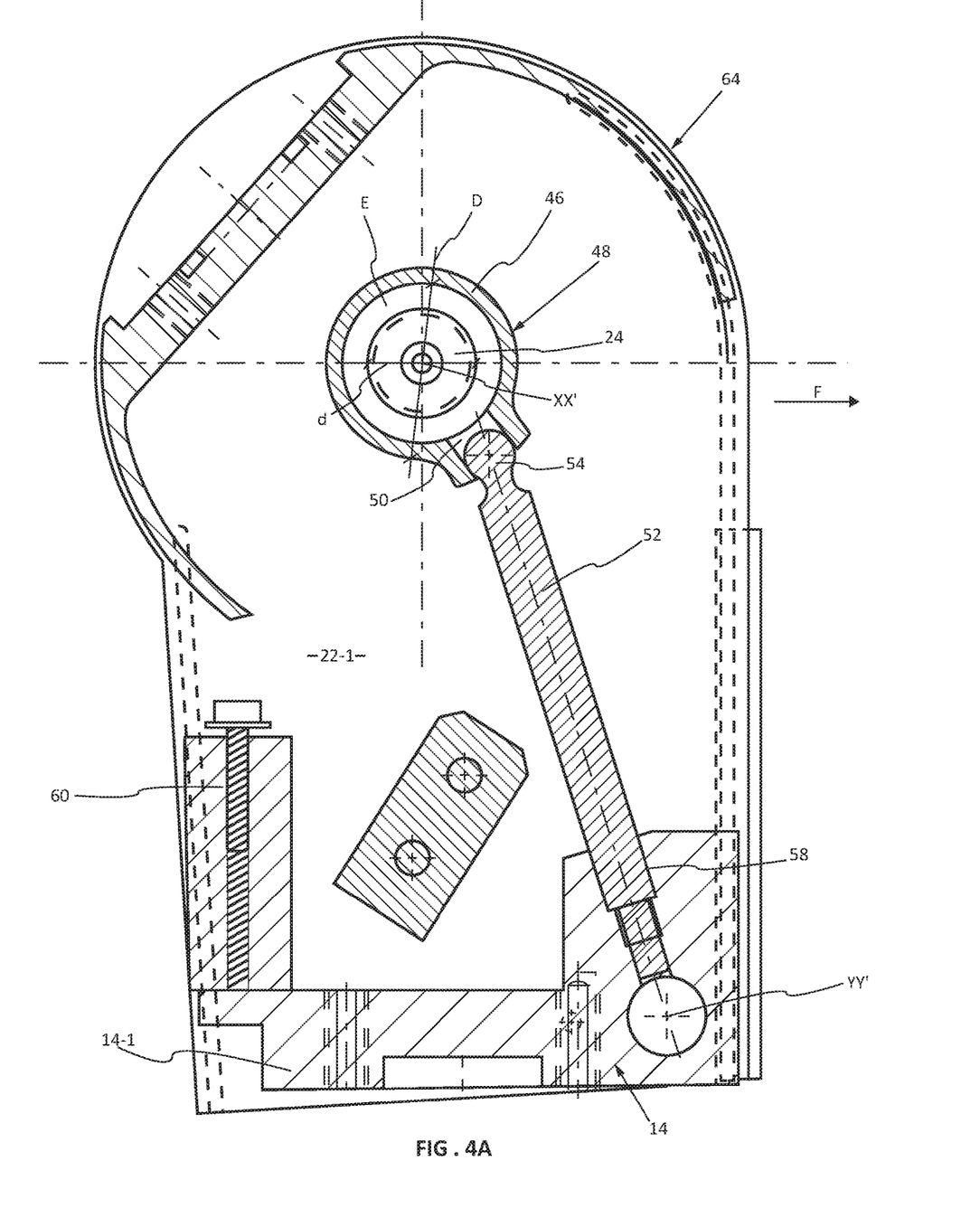
FIGS. 4A and 4B: two sectional views of the prosthesis of FIG. 1 showing the operating connecting rod and the arrangement of the pins of the unlocking means.
Figure 4B:
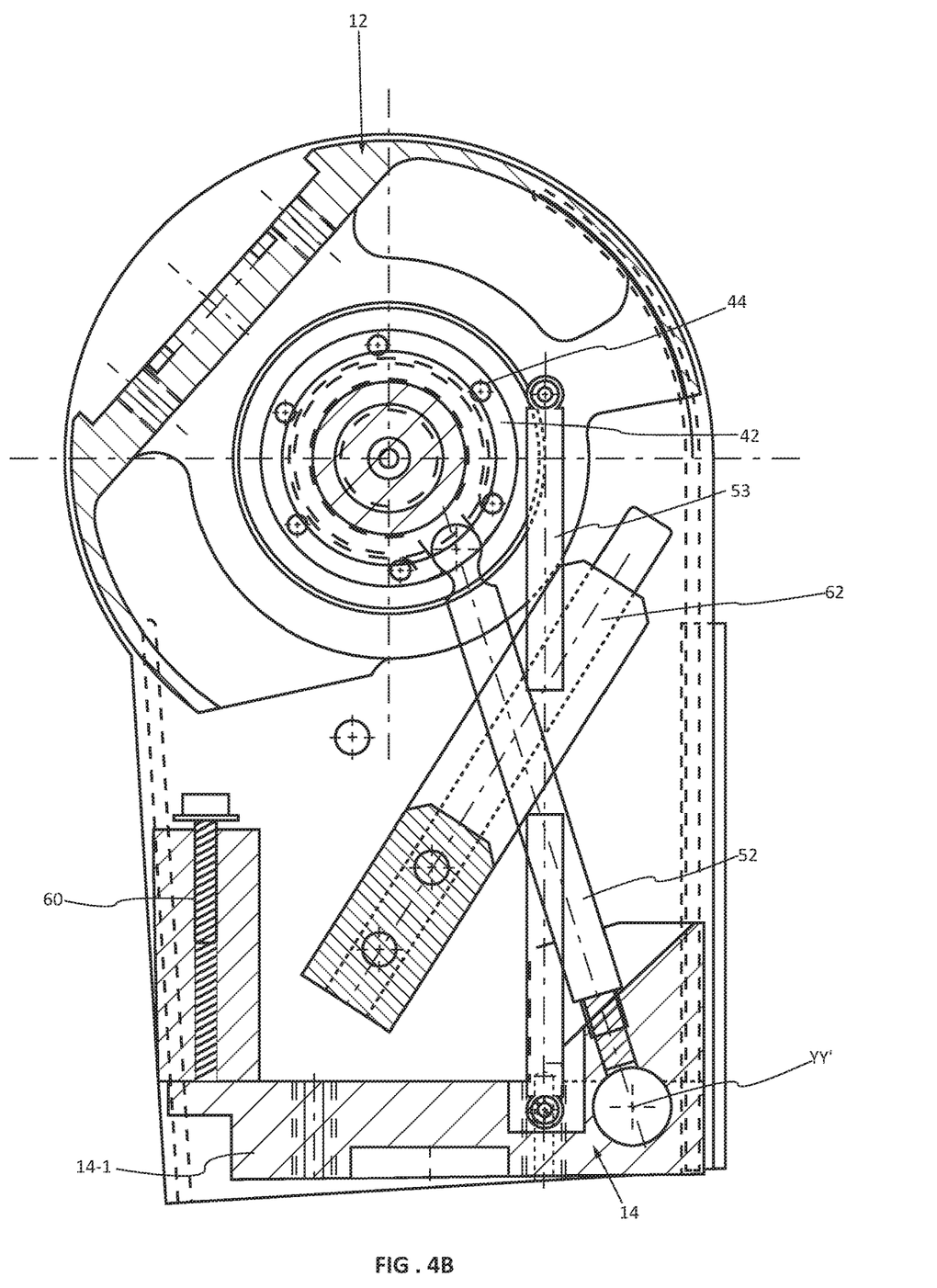

These angular control means 48, as shown in particular in FIG. 4A, comprise a blind patellar housing 50, a connecting rod 52 with a head 54 suitable to work in conjunction, in the form of a ball joint, with the blind patellar housing 50.

The blind patellar housing 50 is radially oriented.

Connecting rod 52 extends to the tibial fixation plate 14-1.

Return means 53, in this case a spring, are interposed between the femoral section 12 and the tibial section 14. In the absence of other forces, particularly inertia, this spring 53 constantly keeps both femoral and tibial sections in alignment. The spring could be an oleo-pneumatic cylinder with adjustment of the return force.

The tibial section 14 therefore comprises flanges 22-1 and 22-2 and pivots about axis XX' and the cylindrical part 16 integral with the femoral section via through-shaft 24.

Tibial plate 14-1 is equipped with connecting means for receiving an artificial tibia, these fixing means comprising a flattened part on the lower surface of the plate, having tapped bores to receive screws, for example.

This tibial fixation plate 14-1 is articulated by a distal edge about an axis YY'defined by a shaft 56, with axis of rotation parallel to axis XX' and placed in front of axis XX' relative to the direction of walking indicated by arrow F. This will be explained in the description of how the device operates.

This plate 14-1 comprises a blind hole 58, oriented radially in relation to the axis YY', designed to rigidly receive the second end of the connecting rod 52. This blind hole 58 receives the connecting rod by screwing, for example, the blind hole 58 then being threaded and the end of the connecting rod being threaded, so as to also allow lengthwise adjustment.

An adjustable stop 60, integral with flanges 22-1 and 22-2, is placed on the proximal edge so as to limit the pivot angle of plate 14-1 upwards and therefore movement of wheel 42 with pins to which it is linked by connecting rod 52. This stop has a screw which makes it possible to finely adjust the stop and also shock absorption systems during contact with the tibial section 14.

This stop 60 is provided with a return spring 61 which pushes plate 14-1 downwards and releases the roller freewheel, as will be detailed in the description of the operation.

Similarly, the angular amplitude of plate 14-1 is limited downwards in order to give the plate an angular freedom of a few degrees.

The device according to the present invention further comprises damper and stop means 62, in the form of a block provided with spring pistons, for example. These stop means 62 are useful in order to reduce the impact on contact and to prevent angular movement of the knee beyond the alignment of the femoral section and the tibial section. These means are not shown in FIG. 1 for the sake of clarity.

The tibial section 14 must always make an angle less than or equal to 180°, as it would naturally.

Similarly, a spacer ring 64 provides the complement with the flange.

It should also be noted that this ring 64, together with wheel 42, provides centering for the rollers, laterally. It would also be possible to replace the rollers with balls. In this case, the question of centering would not arise. The bearing surface of a ball is a point, which may be amply sufficient for the application according to the present invention, but in the context of seeking reliability, a roller has a contact line, namely a peripheral generating line of the roller, so that the load is more evenly distributed, making it the preferred choice in the present invention.

Alternatively, there may also be ball bearings in the free space to improve centering and support of pinion 30 relative to track 20, while taking into account the fact that the prosthesis must be of limited weight.

This makes it possible to reduce friction, operating play and wear related to movements of the knee which are very great in number as soon as the person equipped with the knee begins to walk.

The operation of the locking/unlocking device according to the invention is now described with reference to the block diagram in FIG. 5.

Figures 5A, 5B, 5C, 5D:
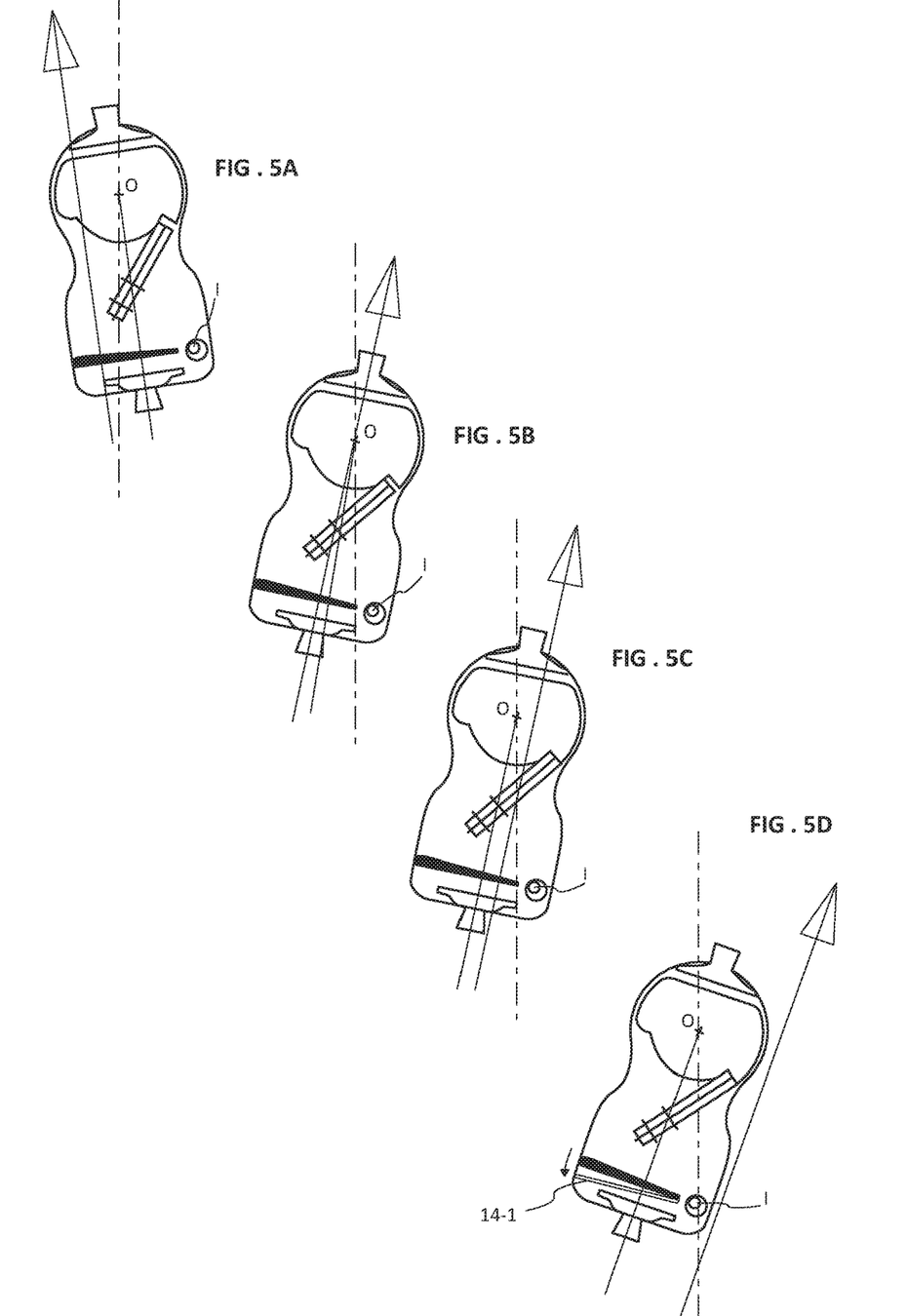
FIGS. 5A to 5G: schematic views during the different operating phases as the wearer walks.

In FIG. 5A, the wearer is in position with his/her leg resting on the ground. Plate 14-1 is pivoted upwards about axis YY', bearing on stop 60. Return spring 61 is compressed, the freewheel is active and locks rotation.

The femoral section and the tibial section are immobilized in the direction of closing the prosthetic knee. The reaction of the ground under the weight of the prosthesis wearer is symbolized by the arrow which is behind point O and point I.

The arrow is therefore behind point O and axis YY' or point I and substantially parallel to the axis passing through point O.

Whenever, as in FIG. 5B, the wearer moves forward, he/she brings the weight to bear on the front and is standing on one foot, on the prosthesis side.

The wearer is still bearing on the ground and the freewheel is still active so the two parts remain immobilized with an imposed alignment of the femoral and tibial section, FIG. 5C. But the assembly has rotated owing to tilting of the wearer's body forward so that the arrow passes in front of point O.

Movement of the prosthesis wearer continues, leading to the diagram of forces shown in FIG. 5D.

The ground reaction tilts forward as the reaction is from the back to the front.

The corresponding arrow, symbolizing this reaction, moves away from point O towards the front, going beyond axis YY' and therefore point I.

This is the last propulsion phase forward just before the double support situation.

Plate 14-1 pivots downwards about this axis YY' via spring 61 of stop 60, connecting rod 52 actuates wheel 42 with its pins 44 which in turn unlock rollers 38: the freewheel is disabled.

The wearer then moves into a situation where the momentum of walking will lead him/her to bring back his/her leg, and this is therefore the beginning of the pendulum or oscillating phase of the prosthetic leg.

Figures 5E, 5F, 5G:
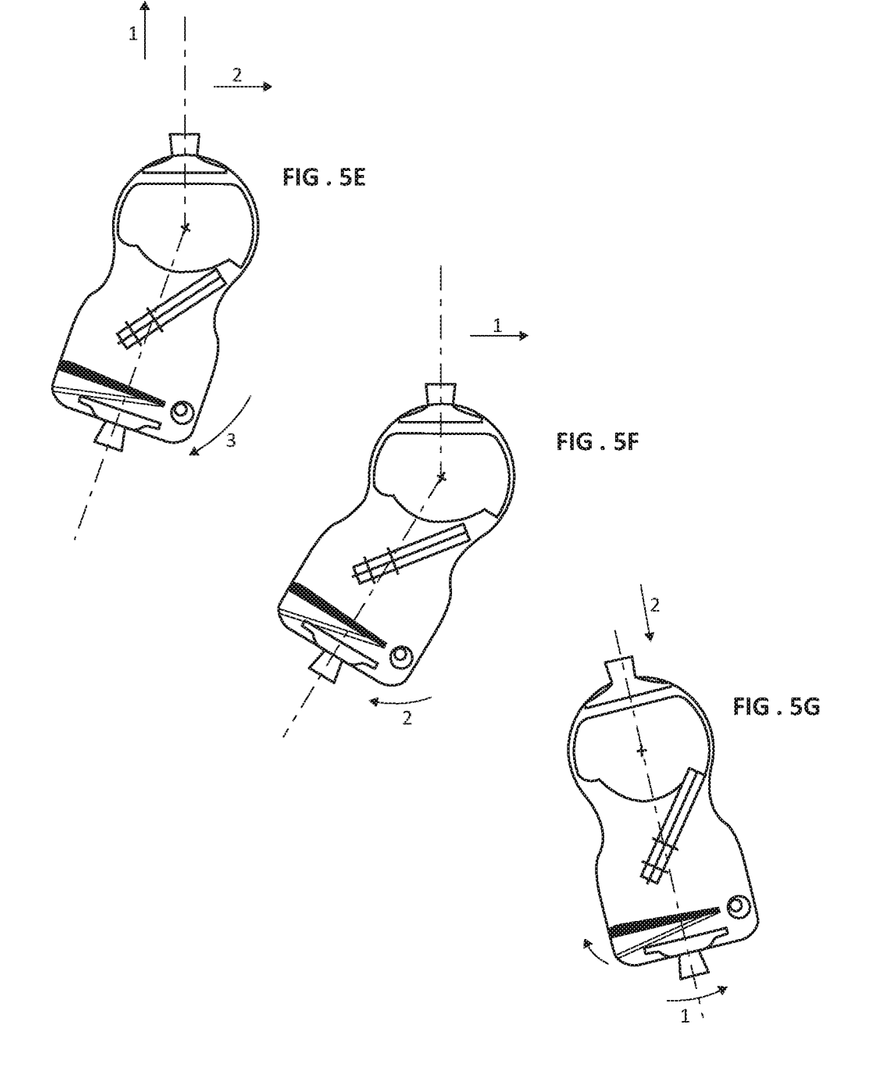
Figure 6:
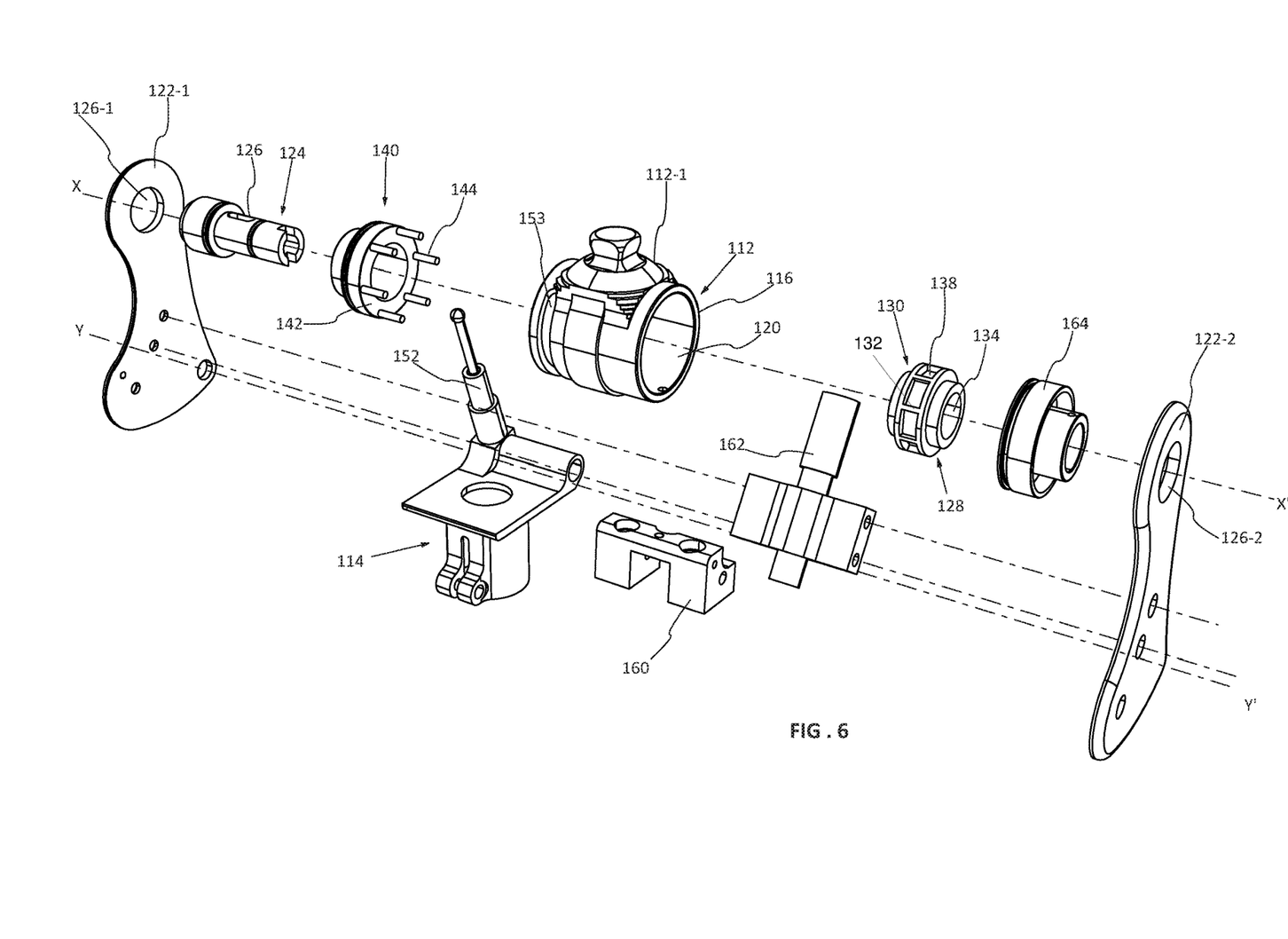
FIG. 6: an exploded perspective view of an alternative embodiment of the mechanism for locking/unlocking the prosthesis.
Figure 7:
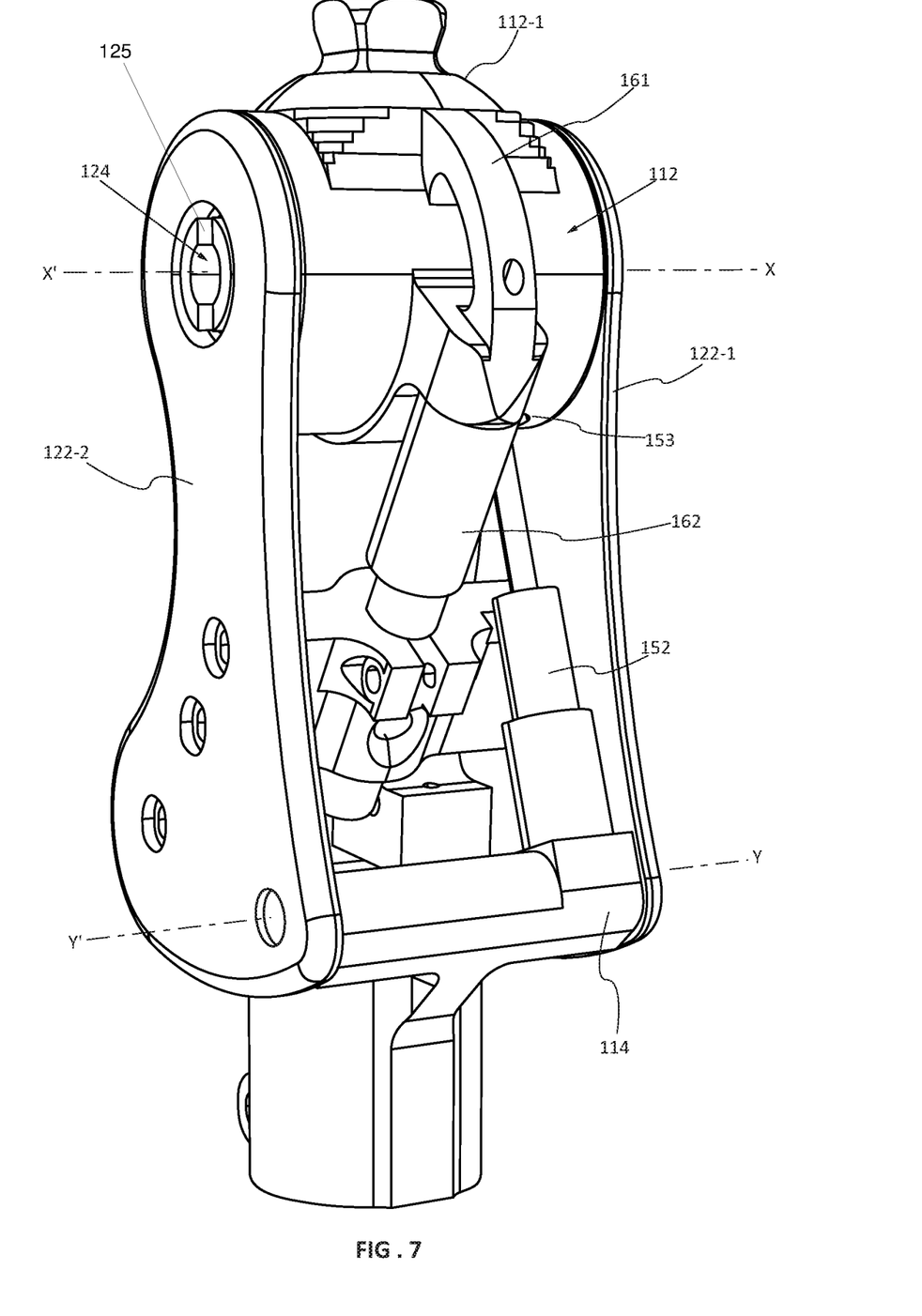
FIG. 7: a front perspective view after assembly.
Figure 8:
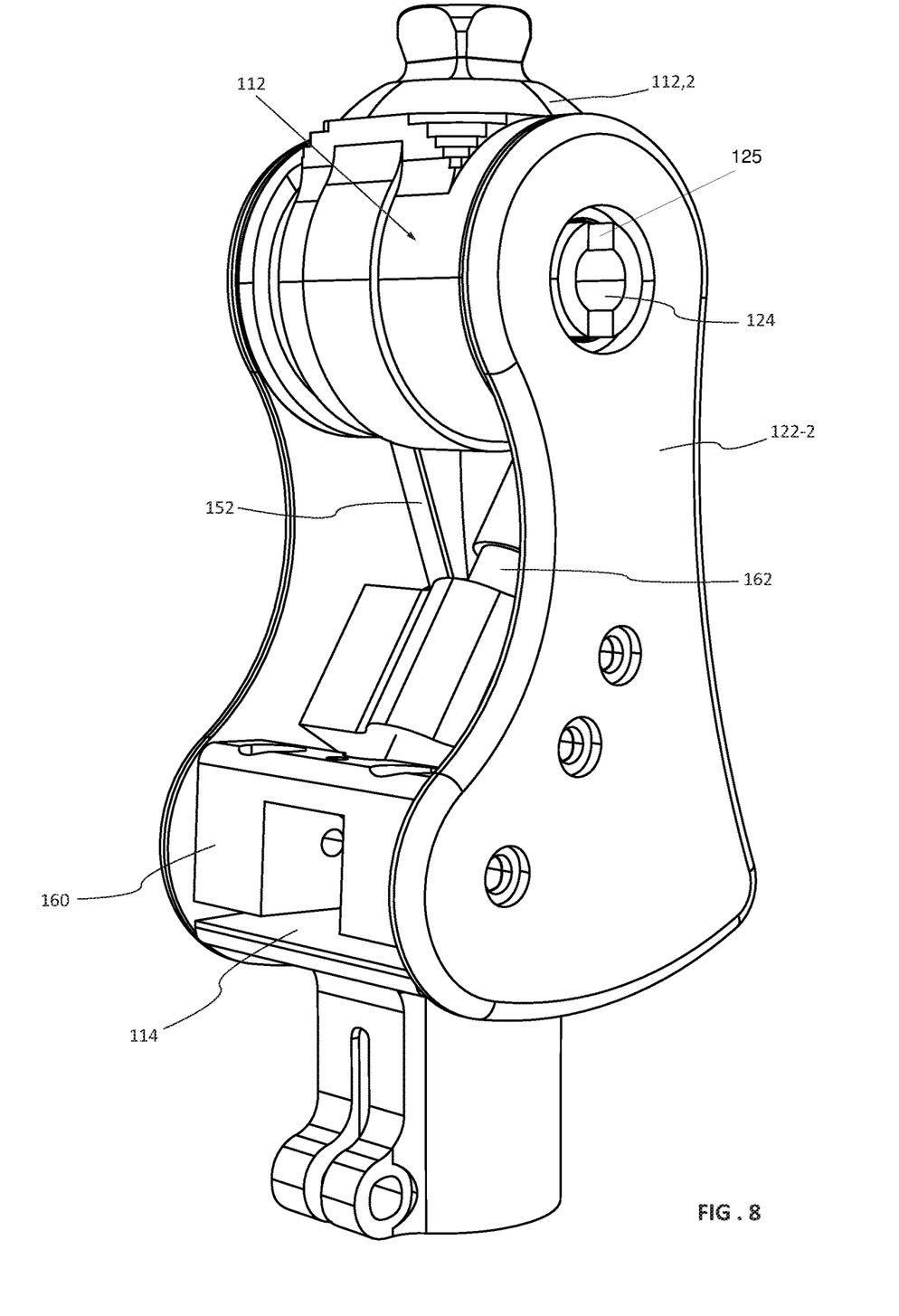
FIG. 8: a rear perspective view after assembly.

Then, in FIG. 5E, after the thrust, the prosthesis wearer lifts the femoral part, but spring 53 ensures that it is initially kept on the ground while maintaining the alignment.

Nevertheless, the return force is quickly overcome by the forces exerted for continuous walking.

The foot then ceases bearing on the ground and the freewheel, already released, can do its work.

Because of this, as a result of the inertia, the femoral section advances more quickly than the tibial section, so that, as in natural walking, both femoral and tibial sections can pivot and the initial 180° angle greatly decreases.

The faster the walk, the more inertia there is, so that the prosthetic knee bend will be all the more natural and aerial.

In FIG. 5F, this maximum bending is easily observed.

In FIG. 5G, the wearer of the prosthesis having moved forward the femoral section, the latter reaches its maximum and the free tibial section comes back towards the front, as a result of gravity, then inertia, with the assistance of spring 53 of the return means.

When the foot is in the required position, the wearer bears on it and again there is angular blocking by locking of the freewheel, with leg extended.

The walking cycle is complete.

It should also be noted that during this phase of bringing back the tibial section, if the wearer, for some reason, were to lean on the equipped leg, bringing his/her foot into contact with the ground would immediately block the freewheel in the angular position that it is in, preventing additional bending and an inevitable fall.

The prosthesis according to the present invention is perfectly safe on all occasions.

The device according to the present invention allows easy locking/unlocking by means of a connecting rod which provides rotational movement of wheel 42 with pins 44 and releases the rollers.

Adjustment problems are easily controlled because of this fixed, screwed connecting rod, of constant length, which can be finely adjustable by screwing, and wearers enjoy easy walking with extremely smooth, natural movements, for an appropriate walking speed.

Unlocking is brought about by movement of the pins 44 caused by release of the return spring 61.

In order to ensure certain locking, the rollers are loaded, in a manner known per se, by a spring, not shown, which tends to permanently push them towards the top of the ramp. Locking of the rollers between the ramp and the track is therefore instantaneous.

These springs are weak and can in no case oppose the thrust forces of the pins 44.

In the preferred embodiment described, a key 36 was used to angularly immobilize the pinion on the through-shaft, but it is also possible to use splines which are a perfectly equivalent means.

This locking/unlocking device according to the invention is advantageous and very reliable.

Adjustment in this embodiment is performed by the stops so that adaptation to the wearer is fast and accurate.

The present invention also makes provision for an alternative embodiment shown in FIGS. 6 to 9.

This variant has many parts identical to those of the embodiment described above; these parts will not be described and will have the same references incremented by 100.

The new parts will have their own references, after the number 100.

In FIGS. 6 to 9, it can be seen that the femoral section 112 includes some modifications of shape and in particular plate 112-1 and the means of connection to the wearer's thigh are directly machined and come from manufacture with the femoral section.

The femoral 112 and tibial 114 sections are still rotatably mounted relative to one another, coaxial about an axis XX', corresponding to the axis of the knee.

Tibial section 114 remains unchanged with the exception of external shapes for appearance.

In the femoral section 112, the technical change consists of a through-shaft 124, which extends across the width and has a groove 125 at its end. This axis passes through both left and right flanges 122-1 and 122-2. This through-shaft 124 is coaxial with axis XX'.

The freewheel assembly 128 is retained, in this case a roller freewheel assembly 138 resting on a ramp 132. Springs may be interposed to press the rollers on the ramp, in a manner known per se and as in the previous embodiment.

Figure 9:
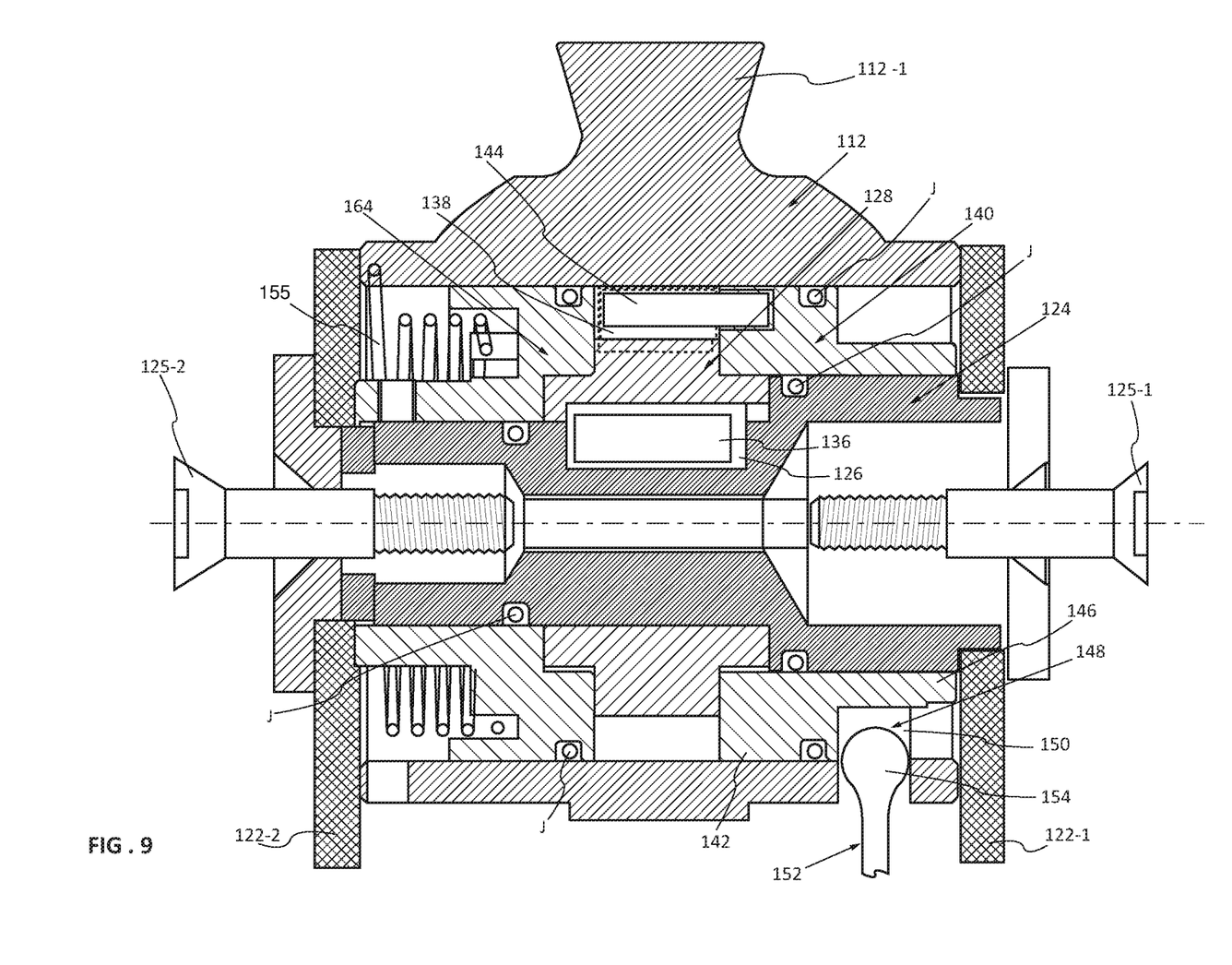
FIG. 9: a sectional view of the patellar part of the prosthesis.

This freewheel assembly 128 is integral with through-shaft 124 via a key 136 which can be seen in FIG. 9, in particular.

This key 136 works in conjunction with a spline 134 of profile conjugate with spline 126 carried by the through-shaft 124.

The means 140 for permanently unlocking rollers 138 are to be found in the form of a wheel 142 with pins 144, mounted coaxial with axis XX' and free to rotate.

The angular control means 148 are kept substantially identical with a blind patellar housing 150, a connecting rod 152 and a head 154 able to work in conjunction with the patellar housing.

The return means 155 are modified as they are in the form of a coil spring, mounted coaxial with axis XX'. The ends of the spring are interposed between the femoral section 112 and the spacer 164.

Similarly, the through-shaft 124 receives two screws 125-1 and 125-2 which are used to assemble the flanges and secure the flanges 122-1 and 122-2 to the shaft 124. This through-shaft is integral with freewheel 128 comprising rollers 138 and ramps 132 via key 136.

Spacer 164 is also integral with the assembly and allows the tibial section 114 to return to opening relative to the femoral section 112, in the absence of strain or blockage.

The unlocking means 140 are free to rotate relative to through-shaft 124 and the associated parts, angular rotation being controlled by connecting rod 152 whose head 154 enters patellar housing 150.

The rod 152 passes through a curvilinear aperture 153, formed in the femoral section 112 to allow rotation of the femoral section without disturbing the operation of the control rod 152 of the unlocking means 140.

This curvilinear aperture 153 may comprise an angularly adjustable stop so as to limit the angular amplitude of the knee, particularly useful when learning to walk again.

The femoral section 112 also has a lip 116 in front of the purely cylindrical section, in order to come to bear on the damping and stop means 162. This lip is integral with the femoral section 112.

The presence of O-rings J may be noted; these are interposed between the rotating parts in order to prevent dust and water from entering.

The tibial section 114 remains identical to that of the main embodiment.

The arrangement so described is smaller in size and this lower spatial requirement means that a smaller prosthesis can be manufactured, finding a direct application for children.

Operation in walking mode as described with reference to the block diagram in FIG. 5 is fully applicable to this variant.

In contrast, provision is made for an improvement applicable to both variants, illustrated schematically in FIG. 10.

This is because when the wearer is seated and his/her leg equipped with the prosthesis is bent at 90°, if he/she wishes to stand up he/she cannot put weight on his/her prosthetic leg.

Means of assistance for standing up from a seated position 66 are therefore also provided so as to allow the patient to rely continuously on his/her prosthetic leg whose knee opens out as the upright position is approached.

These means of assistance for standing up 66 may, for example, take the form of a cam 68, able to take two positions:

the first position 68-1 bearing on connecting rod 52, 152 of the unlocking means to ensure permanent unlocking by means of pins 44, 144 which push each roller 38,138 to the bottom of its ramp, and the second position 68-2, without bearing on connecting rod 52, 152 of unlocking means 40,140 to ensure permanent unlocking allowing the connecting rod 52,152 of the locking means to work in normal operation, as in FIG. 5.

Figure 10A:
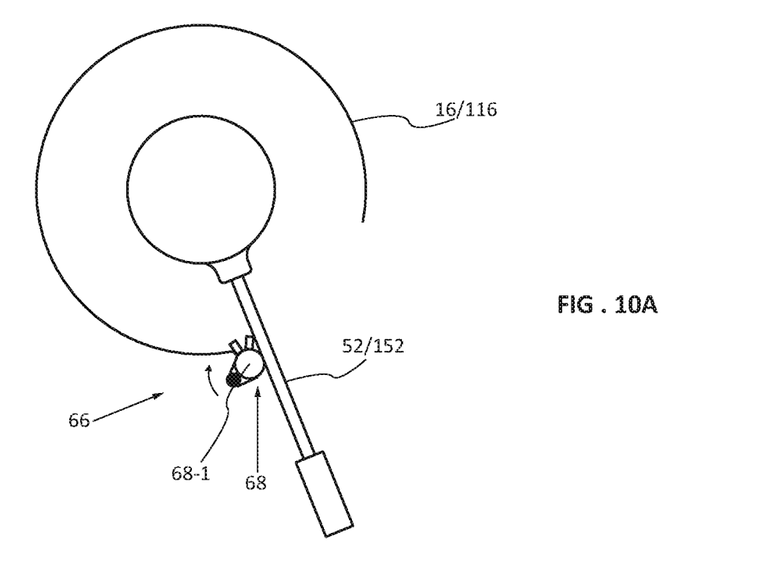
FIGS. 10A and 10B: a schematic view of the arrangement and operation for standing up, with a cam, once the wearer is seated, applicable to both variants.
Figure 10B:
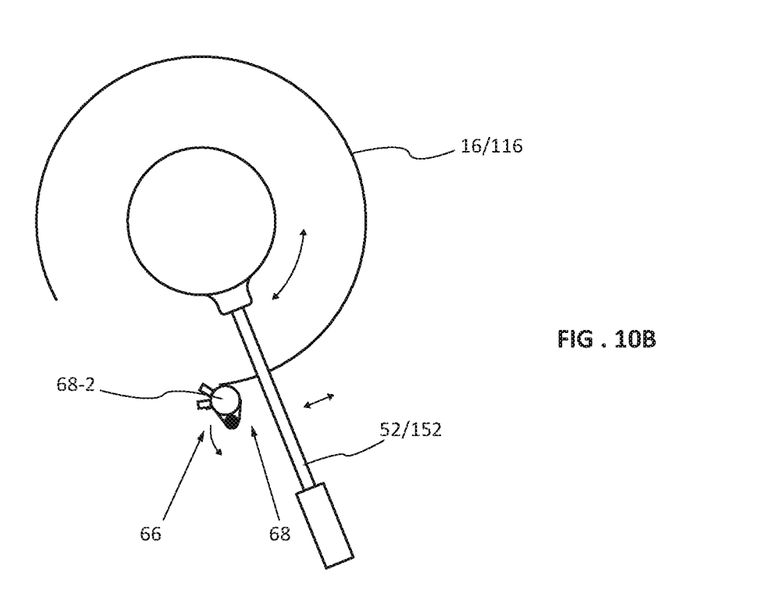

In FIGS. 10A and 10B, such a cam 68 is shown in both positions.

In this way, the movement of the femoral section 12, 112 comes up against the stop in sitting position and actuates the cam via the cylindrical part 16, 116 equipped with a cleat designed to place the connecting rod in the first position. When standing up, the rollers therefore remain unlocked.

In this standing position, the femoral section 12, 112 is substantially in alignment with the tibial section 14, 114.

The cylindrical part 16, 116 via its other side, provided with another suitable cleat, causes cam 68 to move aside. This then releases operation of the prosthesis without any intervention and the wearer can resume normal walking with his/her prosthesis.

In this second variant, note that the through-shaft allows assembly by stacking, allowing parts to be changed independently and therefore servicing of wear parts.

Mounting one of the locking/unlocking devices described by stacking and interlocking is within the reach of medical personnel, requiring little additional qualification in mechanics or the use of sophisticated tools.

Replacement of potentially worn or faulty parts is very quick.

It should also be noted that the dimensions of the parts are reduced so that the prosthesis itself, provided with one of the locking/unlocking devices, is lighter.

Such a prosthesis, whatever the variant, is perfectly suitable for applications for children.

In addition, the outer design of the flanges and the femoral section can very easily be adapted to suit the wearer.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The invention claimed is:

1. A locking/unlocking device for a knee prosthesis, comprising a femoral section configured to be connected to the wearer's thigh, and a tibial section provided with a tibial plate articulated about a first axis, configured to receive an artificial tibia and foot, these two femoral/tibial sections being both mounted rotatably, coaxial about a second axis, the first and second axes being parallel, corresponding to an axis of bending of a natural knee, comprising:
    a cylindrical part comprising the femoral section, with a central, cylindrical housing arranged coaxially with the second axis and comprising a track,
    two left and right flanges and a single through-shaft, coaxial with the second axis, comprising the tibial section,
    a freewheel assembly comprising a pinion provided with ramps and one rolling member per ramp, said freewheel assembly being interposed between the track and the single through-shaft,
    unlocking means comprising a wheel with pins, also mounted coaxially with the second axis, the pins being interposed between the track and the ramps on the pinion, and
    a section offset from the unlocking means comprising angular control means comprising at least one connecting rod interposed between said offset section and the tibial plate.

2. The locking/unlocking device for a knee prosthesis according to claim 1, wherein the connecting rod comprises a head at one end, the offset section comprises a blind patellar housing receiving said head, and wherein the tibial plate comprises a blind hole configured to rigidly receive the second end of the connecting rod.

3. The locking/unlocking device for a knee prosthesis according to claim 2, wherein the blind hole is oriented radially with respect to the first axis.

4. The locking/unlocking device for a knee prosthesis according to claim 1, wherein the tibial plate is articulated by a distal edge around the first axis about a shaft placed in front of the second axis with respect to a direction of walking and passing through both left and right flanges.

5. The locking/unlocking device for a knee prosthesis according to claim 1, further comprising an adjustable stop integral with the left and right flanges, placed at a proximal edge of the tibial plate so as to limit a pivot angle of said plate upwards.

6. The locking/unlocking device for a knee prosthesis according to claim 1, further comprising a damping and stop means to avoid angular movement of knee beyond an alignment of the femoral and tibial sections.

7. The locking/unlocking device for a knee prosthesis according to claim 1, wherein the rolling members comprise rolling balls and the ramps comprise bowls.

8. The locking/unlocking device for a knee prosthesis according to claim 1, wherein the rolling members comprise rollers.

9. The locking/unlocking device for a knee prosthesis according to claim 1, wherein the through-shaft comprises a spline, wherein the pinion with ramps of the freewheel assembly comprises a spline, and wherein a key is interposed between the two splines so as to angularly immobilize said pinion with ramps on said shaft.

10. The locking/unlocking device for a knee prosthesis according to claim 1, further comprising return means interposed between the femoral section and the tibial section so as to maintain alignment between said two sections and to provide return assistance.

11. The locking/unlocking device for a knee prosthesis according to claim 10, wherein the return means comprise a coil spring interposed on a spacer between said spacer and the femoral section.

12. The locking/unlocking device for a knee prosthesis according to claim 11, wherein the femoral section comprises a curvilinear aperture configured to allow the connecting rod through.

13. The locking/unlocking device for a knee prosthesis according to claim 12, wherein the curvilinear aperture comprises an angularly adjustable stop to limit an angular amplitude of the knee.

14. The locking/unlocking device for a knee prosthesis according to claim 1, wherein assistance means are provided for standing up from a sitting position comprising a cam configured to take up two positions:

in a first position, the cam presses on the connecting rod of the unlocking means to ensure permanent unlocking by means of the pins which push each roller rolling member to the bottom of its ramp, and in the second position, the cam, without pressing on the connecting rod of the unlocking means, allows the connecting rod of the locking means to work in normal operation.

* * * * *